U S 0 0 8 1 5 3 3 8 1 B 2

US008153381B2

(12) United States Patent
Palin et al.

(10) Patent No.: US 8,153,381 B2
(45) Date of Patent: Apr. 10, 2012

(54) METHODS FOR DETECTION OF THE STRAIN OF A PATHOGEN

(75) Inventors: William J. Palin, Cape Elizabeth, ME (US); Nathan Turner, Portland, ME (US)

(73) Assignee: Alere Scarborough, Inc., Scarborough, ME (US)

( * ) Notice: Subject to any disclaimer, the term of this patent is extended or adjusted under 35 U.S.C. 154(b) by 629 days.

(21) Appl. No.: 12/110,874

(22) Filed: Apr. 28, 2008

(65) Prior Publication Data

US 2008/0293041 A1 Nov. 27, 2008

Related U.S. Application Data

(63) Continuation-in-part of application No. PCT/US2006/042146, filed on Oct. 30, 2006.

(60) Provisional application No. 60/731,088, filed on Oct. 28, 2005.

(51) Int. Cl.
*G01N 33/53* (2006.01)

(52) U.S. Cl. ....... 435/7.1; 435/7.93; 435/7.94; 435/7.95

(58) Field of Classification Search .......................... None
See application file for complete search history.

(56) References Cited

U.S. PATENT DOCUMENTS

| 3,496,066 A | 2/1970 | Berger et al. |
| 4,925,789 A | 5/1990 | Edberg |
| 7,465,587 B2 * | 12/2008 | Imrich ........................... 436/514 |
| 2003/0119203 A1 | 6/2003 | Wei et al. |
| 2007/0224594 A1 | 9/2007 | Lu et al. |

FOREIGN PATENT DOCUMENTS

| WO | WO-2005/007697 | 1/2005 |
| WO | WO-2007/053487 | 5/2007 |

OTHER PUBLICATIONS

Philpott, M., et al.; "Neutralizing epitopes of the H5 hemagglutinin from a virulent avian influenza virus and their relationship to pathogenicity," J. Virol. 1989, vol. 63(8), p. 3453-8.
Shelburne, SA, et al. "Growth characteristics of and Virulence Factor Production by Group A *Streptococci* during cultivation in Human Saliva," *Infect Immunity* 2005, 73, 4723-4731.
Tkacova, M. and Vareckova, E.; A sensitive one-step immunocapture EIA for rapid diagnosis of influenza A,: J. Virol Methods, 1996, vol. 60(1), pp. 65-71.
Walls, H., et al.; "Characterization and evaluation of monoclonal antibodies developed for typing influenza A and influenza B viruses," J. Clin. Microbiol. 1986, vol. 23(2), pp. 240-245.
Wellstood, SA. "Rapid, cost-effective identification of Group A *Streptococci* and *Enterococci* by L-pyrrolidonyl-beta-naphthylamide hydrolysis," *J. Clin. Microbiol.* 1987, 25, 1805-1807.
ISR from PCT/US06/42146 (WO 2007/053487) mailed Nov. 19, 2008.

* cited by examiner

*Primary Examiner* — Bao Thuy L Nguyen
(74) *Attorney, Agent, or Firm* — Foley Hoag LLP

(57) ABSTRACT

Provided are methods and devices for determining the strain of a pathogen in a sample.

3 Claims, 4 Drawing Sheets

FIGURE 1

Influenza A H3N2 Inhibition Experimental Trial: Results

No Latex Control | Goat α-Rabbit Latex | Mouse α-H3N2 Latex

FIGURE 2

Influenza A Novel Method
H3N2 Model vs. H1N1

ICT Control         Goat α-Rabbit         Mouse α-H3N2
                       Latex                  Test

METHODS FOR DETECTION OF THE STRAIN OF A PATHOGEN

RELATED APPLICATIONS

This application is a continuation-in-part application of PCT/US06/042146, filed Oct. 30, 2006, which claims the benefit of priority to Provisional Application 60/731,088, filed Oct. 28, 2005, which is hereby incorporated by reference in its entirety.

FIELD OF INVENTION

The present invention relates generally to the field of detection methods for specific pathogen strains.

BACKGROUND OF THE INVENTION

A primary interest in being able to detect a target of interest is to detect pathogens including viruses, bacteria, and compounds, which are able to cause discomfort or disease in human or animal populations. One area of particular interest is to have a diagnostic kit for detecting the avian influenza virus. Diagnostic tests take years to develop and optimize, are subjected to rigorous clinical trials and regulatory requirements and once manufactured are valid only during their designated shelf life. In the instance where a clinically significant variation in the target for such a test is predicted or shown to sporadically arise, heretofore, a separate test must be designed to specifically detect that variant, that is the strain. In light of the long development timeline and the inability to predict demand for such a test, commercial diagnostic manufacturers may be reluctant to undertake development regardless of the potential benefits to society.

A model for such variations is the avian strains of influenza type A (FluA). Should one of these avian strains develop virulence for transmission in the human population the public health consequence could be severe as was seen in the 1918 "Spanish Flu" global pandemic. However, the H5N1 strain of avian influenza first detected in Hong Kong in 1997 has not yet developed such virulence and has remained almost entirely in the avian population for 8 years. While development of a general test for influenza type A is easily justified as various strains circulate every year, development and manufacture of a test specific for any single strain, such as H5N1, encompasses significant risk as it may not arise within the shelf life of the test.

The proactive development of a stable variant-specific ancillary detection method for use with existing nondiscriminatory tests in the field that could be rapidly deployed in the event of an outbreak would minimize the risk associated with esoteric variant-specific test development are desirable and allow for greater public safety.

SUMMARY OF THE INVENTION

Provided are methods and devices for detecting the strain, i.e. a variant, of a generic pathogen of interest. Variant-specific information is obtained by contacting the sample with antibodies specific to the variant or strain-specific portion of a pathogen to generate antibody-pathogen complexes and removing these complexes from the sample by any of several known methods. The treated sample is then contacted with antibodies specific for a non-variant (that is, conserved among strains) portion of the pathogen to generate complexes if any pathogen remains in the sample, and the absence of detection of such complexes is indicative of the presence of the specific variant or strain.

For example, some embodiments include a device comprising a carrier defining a flow path extending at least from a sample receiving zone to a detection zone, immobilized first antibodies specific for a variant-specific portion of a pathogen of interest disposed along the flow path, immobilized second antibodies specific for a non-variant-specific portion of the pathogen of interest; and wherein a liquid sample comprising a pathogen received by the receiving zone migrates along the flow path on which the first antibodies are immobilized, and if the pathogen is of the variant for which the first antibodies are specific, the first antibodies capture the pathogen along the flow path and remove it from the sample prior to it reaching the detection zone.

In another embodiment, a device comprises a carrier defining a flow path extending at least from a sample receiving zone to a detection zone, immobilized first antibodies specific for a non-variant-specific portion of a pathogen of interest disposed along the flow path, immobilized second antibodies specific for a variant-specific portion of the pathogen of interest; and wherein a liquid sample comprising a pathogen received by the receiving zone migrates along the flow path on which the first antibodies are immobilized, and if the pathogen is of the non-variant for which the first antibodies are specific, the first antibodies capture the pathogen along the flow path and remove it from the sample prior to it reaching the detection zone.

The methods may be incorporated into any test format or device suitable for the practice of the methods. Also provided are kits, reagents, etc. for the practice of the methods.

Further objectives and advantages of the present invention will become apparent as the description proceeds. To gain a full appreciation of the scope of the present invention, it will be further recognized that various aspects of the present invention can be combined to make desirable embodiments of the invention.

BRIEF DESCRIPTION OF THE FIGURES

FIG. 1 shows the anti H3 latex particles of the assay described in Example 1 have successfully immobilized a sufficient quantity of the H3N2 virus to extinct the signal in the FluA test.

FIG. 2 shows that the assay of Example 1 is hemagglutinin strain specific.

DETAILED DESCRIPTION OF THE INVENTION

Figure 3A:
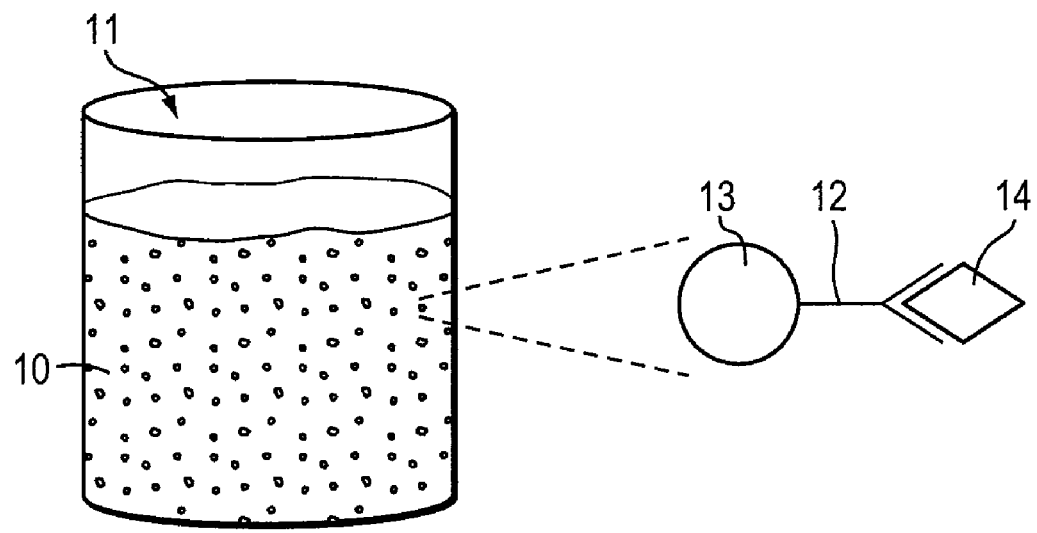
FIG. 3a shows a container containing a sample, and a complex formed by an antibody and a variant-specific portion of a pathogen.

Unless defined otherwise above, all technical and scientific terms used herein have the same meaning as commonly understood by one of ordinary skill in the art to which this invention belongs. Where a term is provided in the singular, the inventor also contemplates the plural of that term. The nomenclature used herein and the procedures described below are those well known and commonly employed in the art.

The term "antibody" refers to an immunoglobulin, derivatives thereof which maintain specific binding ability, and proteins having a binding domain which is homologous or largely homologous to an immunoglobulin binding domain.

These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In exemplary embodiments, antibodies used with the methods and compositions described herein are derivatives of the IgG class.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The terms "comprise" and "comprising" is used in the inclusive, open sense, meaning that additional elements may be included.

The term "including" is used herein to mean "including but not limited to". "Including" and "including but not limited to" are used interchangeably.

The term "non-variant-specific portion" means a region of a pathogen, i.e. a particular protein sequence, protein fold, nucleic acid sequence, etc. that is not present on a particular variant of a pathogen of interest.

The term "pathogen" refers to any organism which may cause disease in a subject, such as a bacterium, fungus, parasite, virus, etc.

The term "sample" refers to any sample potentially containing a pathogen. For example, a sample may be a bodily fluid such as blood, urine or saliva.

A "variant" of a pathogen, as used herein, refers to a version of the pathogen that results from mutation or natural variation, i.e., a strain.

A "variant-specific portion" means a region of a pathogen, i.e. a particular protein sequence, protein fold, nucleic acid sequence, etc. that is present only on a particular variant of a pathogen of interest.

Provided are devices and methods for detecting a target of interest such as pathogens including virus, bacteria, fungi, or any distinct portion or fragment thereof or other types of compounds that are able to cause discomfort or disease in human or animal populations can be made cost effective and be rapidly deployed in the event of an outbreak.

The methods and devices comprise the use of one or more antibodies or antibody fragments specific for one or more distinct epitopes of a pathogen to differentiate among variants, or strains, of the pathogen that may be separately detected by one or more epitopes common to all of the variants of the pathogen.

In one embodiment, a method for detection of a variant-specific pathogen, i.e., strain, of interest comprises the steps of providing a sample, preferably a liquid sample, known to contain the pathogen, whose strain is as of yet unidentified. The pathogen of interest can be any pathogen capable of being detected, a bacterium, virus, fungus, or any distinct portion or fragment thereof. A sample can be tested by any known methods in order to confirm the presence of the generic pathogen in the sample. For example, a sample suspected of containing a specific strain of the influenza virus can be tested by performing an immunoassay, sandwich immunoassay, competitive immunoassay, simultaneous immunoassay, nucleic acid detection, PCR, gPCR, enzyme assay, or a combination thereof on said sample. By way of example a general immunochromatographic test device that is able to detect a Influenza type A may be used in order to confirm that the sample contains some variant of the influenza virus.

The methods may also include providing an antibody or antibody fragment specific for a variant-specific portion of the pathogen of interest, as show in FIG. 3a. Container 11 contains a mixture including an amount of sample 10 and a variant-specific antibody or antibody fragment 12 bound to a particle or other surface 13. The variant-specific antibody or antibody fragment 12 binds to the variant-specific portion of the pathogen 14, if present, to form complexes 15. In the event that the pathogen 14 does not contain the variant-specific portion, no complex is formed and the pathogen 14 remains in the sample 10.

Figure 3B:
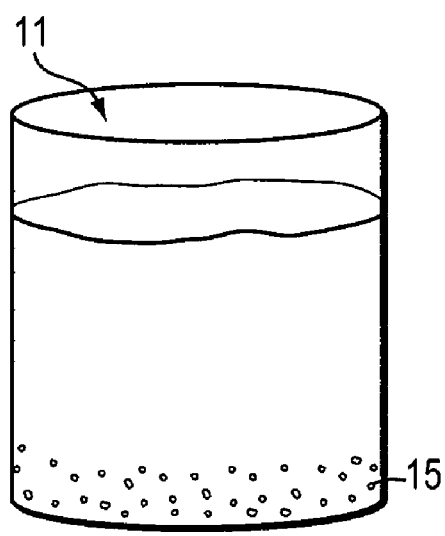
FIG. 3b shows the container of FIG. 3 after centrifugation.

If present, the variant-specific antibody-pathogen complexes 15 may be removed from the sample 10 by any removal method suitable for removing all or substantially all of the complexes 15 from the sample mixture 10. As shown in FIG. 3b, sample 10 is centrifuged to separate variant-specific antibody-pathogen complexes 15 and any non-variant pathogen. By way of example, the removal methods include removal by way of filtration, centrifugation, size exclusion chromatography, gravimetric, phase, reverse phase, polyethylene glycol-precipitation, magnetic, or a combination thereof.

Figure 4:
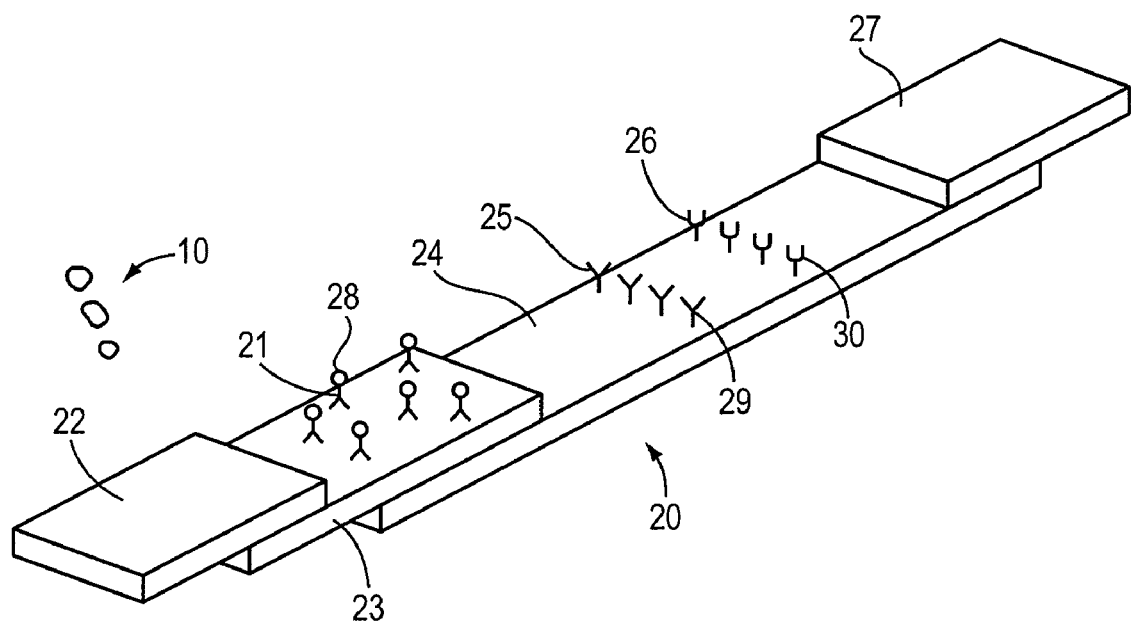
FIG. 4 shows an immunoassay device.

Referring to FIGS. 3 and 4, the methods further comprise contacting the sample 10 with a second antibody or antibody fragment 21 specific for a non-variant portion of the pathogen 14. The second antibody or antibody fragment 21 may be labeled for ease of detection, and the label 28 can be any suitable label that is able to be detected. By way of example, the label 28 may be radiolabel, fluorescent label, or particulate label such as latex particles, dyes, or sols.

In the event that the sample 10 contains a pathogen 14 having the variant-specific portion, the variant-specific antibody or antibody fragment 12 binds the pathogen 14, forming complexes, which will be removed from the sample mixture 10 in the removal step and no pathogen 14 will thus be available for the second antibody or antibody fragment 21 to bind leaving the non-variant specific antibody 21 unbound. However, in the event that the pathogen 14 does not contain the variant-specific portion, but is another variant, the variant-specific antibody or antibody fragment 12 does not bind anything and no complex is formed. However, the non-variant-specific antibody or antibody fragment 21 is able to bind to the conserved or non-variant portion or epitope of the pathogen 14 to form complexes.

The methods may further comprise detecting the presence or absence of the non-variant-specific antibody-pathogen complexes, wherein the absence of such complexes indicative of the presence of the variant-specific pathogen of interest. In the detection step, the sample mixture can be tested by any known methods able to detect the complexes. By way of example, the detection methods may include performing an immunoassay, sandwich immunoassay, competitive immunoassay, simultaneous immunoassay, nucleic acid detection, PCR, gPCR, enzyme assay, or a combination thereof on the sample. For example, the sample can be tested by a general immunochromatographic test device that is able to detect influenza type A. In the event that the sample originally contained the variant-specific target, the detection method would not be positive because the removal of the variant-specific antibody-pathogen complexes out of the sample would have removed all or substantially all of the pathogens from the sample and the non-variant-specific antibodies or antibody fragments would not able to bind any pathogens to form complexes to be detected. A negative result or the absence of a positive result in the detection step means that the variant-specific pathogen was originally present in the sample. A positive result in the detection step means that the variant-specific pathogen of interest was not originally present in the sample, but another version of the pathogen was present.

In one embodiment, a method may comprise: a) contacting a sample 10 comprising a pathogen 14 with a first antibody 12 specific for a variant-specific portion of the pathogen, wherein a pathogen-first antibody complex 15 is formed if the variant-specific portion is present on the pathogen 14 in the sample 10; b) removing the pathogen-first antibody complexes from said sample 10, if present; c) contacting the sample 10 with a second antibody 21 specific for a non-variant-specific portion of the pathogen, wherein a pathogen-second antibody complex is formed if the pathogen is still present in the sample; and d) detecting the presence or absence of the second pathogen-antibody complexes; wherein the absence of said second pathogen-antibody complex indicates that the pathogen is of the variant for which the first antibody is specific. In certain embodiments, the pathogen is influenza type A. In such embodiments, the first antibody may be selected from the group consisting of: an anti-H3 antibody and an anti-H5 antibody.

For use in the diagnostic and other applications suggested above, kits and devices for the practice of the above-described methods are also provided. Devices for practice of the methods include lateral flow devices (wherein the reagents employed in the reaction may be dried onto the chromatographic support contained within the device), a test strip, or other support for practice of the methods. A kit may include a nucleic acid template, a antibody specific for ribosomes of a pathogen of interest, a support, and wash and incubation buffers. Such kits and devices can contain any number or combination of reagents or components. The kits can comprise one or more of the above components in any number of separate containers, tubes, vials and the like or such components can be combined in various combinations in such containers. Kit components may be packaged for either manual or partially or wholly automated practice of the foregoing methods. Further, instructions for the use of a device or kit may be included with the device or kit. Such kits and devices may have a variety of uses, including, for example, diagnosis, therapy, and other applications.

Referring to FIG. 4, by way of example, generally, an immunoassay device 20 for determining the presence or amount of an analyte of interest in a sample 10 includes a sample application member 22, which is in liquid communication with a conjugate pad 23, which is in liquid communication with a nitrocellulose test strip 24 having a test result zone 25 and a control zone 26. The immunoassay device 20 can also include a distal sink 27 at the end opposite to the sample application pad 22 to absorb any excess liquid after testing has run to completion.

The sample application pad 22 is a porous pad able to absorb the sample 10 to be tested and transfer the absorbed sample 10 to the conjugate pad 23 by capillary action. The conjugate pad 23 includes one or more dried molecules or reagents, such as antibodies 21, containing a label 28. The antibodies 21 are capable of specifically binding to the one or more analytes of interest forming an analyte-labeled reagent complex. The conjugate pad 23 may also include one or more stabilizing compounds that are able to induce thermal stability and also stability as to conditions imposed by humidity and temperature. The conjugate pad 23 is a porous pad able to absorb the transferred sample 10 from the sample application pad 22 and transfer the sample 10 to the nitrocellulose strip 24 by capillary action. The nitrocellulose strip 24 is able to absorb the sample 10 from the conjugate pad 23 and transfer the sample 10 by capillary action downstream to the test result zone 25 and the control zone 26. The test result zone 25 of the immunoassay device 20 includes one or more immobilized molecules or reagents, such as antibodies or antibody fragments 29, capable of specifically binding to the one or more analytes of interest or any portion of the analyte-labeled reagent complex. The control zone 26 of the immunoassay device 20 may include one or more immobilized molecules or reagents, such as antibodies or antibody fragments 30, capable of specifically binding to the one or more labeled reagent.

When a liquid test sample 10 is applied to the sample application pad 22 of the device 20, the sample 10 travels through the sample application pad 22, the conjugate pad 23, and nitrocellulose strip 24 by capillary action. When the sample 10 travels through the conjugate pad 23, the sample solubilizes the dried labeled molecule or reagent 21, and if the analyte of interest is present in the sample, the solublized labeled molecule or reagent 21 binds the analyte of interest forming an analyte-labeled reagent complex, otherwise, if the analyte of interest is not present in the sample, no complex is formed. For example, the analyte of interest may be a pathogen, and the reagent can bind to a variant-specific or non-variant specific portion of the pathogen. The analyte-labeled reagent complex in the case of a positive test, or the labeled reagent alone in the case of a negative test, then travel to the nitrocellulose strip 24 and travel through and pass the test result zone 25 and the control zone 26 of the device 20. If the analyte of interest is present in the sample, the analyte-labeled reagent complex binds to the immobilized reagent 29 of the test result zone 25 forming a detectable line, and if the analyte of interest is not present in the sample, no analyte labeled reagent complex is formed and therefore no binding occurs at the test result zone. Whether or not the analyte of interest is present in the sample to form a complex, the labeled reagent 21 binds to the immobilized reagent 30 of the control zone 26 forming a detectable line indicating that the test has run to completion. Any excess liquid sample, after the testing has run to completion, can be absorbed the distal sink 27 of the device.

As disclosed herein, a sample may be contacted with a first antibody is specific for a variant-specific portion of the pathogen, and a second antibody specific for a non-variant specific portion of the pathogen. The first antibody is used to remove pathogens having a variant-specific portion from the sample. The remaining sample, free of variant-specific portion of the pathogen, is contact with the second antibody, specific for a non-variant specific portion of the pathogen. Alternatively, a sample may be contacted with first antibody specific for a non-variant specific portion of the pathogen, and a second antibody specific for a variant-specific portion of the pathogen. An example of such a method may comprise: a) contacting a sample comprising a pathogen with a first antibody specific for a non-variant specific portion of the pathogen, wherein a pathogen-first antibody complex is formed if the pathogen is present in the sample; b) removing the pathogen-first antibody complexes from said sample, c) contacting the sample with a second antibody specific for a variant-specific portion of the pathogen, wherein a pathogen-second antibody complex is formed if the variant-specific portion is present on the pathogen in the sample; and d) detecting the presence or absence of the second pathogen-antibody complexes; wherein the absence of said second pathogen-antibody complex indicates that the pathogen is of the non-variant for which the first antibody is specific. Any of the methods, assays and kits described herein may be practiced in such a form.

EXEMPLIFICATION

The invention, having been generally described, may be more readily understood by reference to the following examples, which are included merely for purposes of illustration of certain aspects and embodiments of the present invention, and are not intended to limit the invention in any way. All headings are for the convenience of the reader and should not be used to limit the meaning of the text that follows the heading, unless so specified.

Example 1

Method of Detecting Influenza A Strain H3N2

The H3N2 strain of the avian influenza A virus and anti H3 serotype monoclonal antibodies were used in this example. An inactivated H1N1 strain was used as the non-serotype control.

The Binax NOW™ Influenza A rapid colloidal gold immunoassay test, capable of detecting H3N2, H1N1 and H5N1 strains, was used as the general assay in the model. Anti-H3 specific monoclonal antibody (Chemicon, part # MAB8254) was obtained and conjugated by passive adsorption to latex particles (Bangs Labs Cat Code DCOOB, Lot #3602, Blue, 0.85 um). H3N2 FluA strain A/Hong Kong/8/68 was obtained from ATCC and serial dilutions were tested to determine an appropriate sample concentration. All manipulations and testing of live FluA virus was performed under a biological containment hood in a dedicated biohazard lab following universal biosafety precautions.

In this experiment, 50 µl each of 1% mouse α-H3 latex particles, 1% goat α-rabbit latex particle control (Merlin Labs, lot 22705A) and assay diluent to serve as a no latex control were aliquotted into separate microfuge tubes. 100 µl of a 1:133 dilution of H3N2 FluA was added to each (final dilution 1:200.) All samples were incubated at 37° C. and shaken at 200 RPM for 30 min. Samples were subsequently 0.2 µm filtered and run on the FluA test. FIG. 1 shows that the anti H3 latex particles have successfully immobilized a sufficient quantity of the H3N2 virus to extinct the signal in the FluA test. By contrast, incubation with the control latex does not affect the signal indicating that the phenomenon observed is H3 specific and not a result of nonspecific binding of virus to latex.

Example 2

Validation of Example 2

As a further validation of the invention in this model the same Example 1 was undertaken using the H1N1 FluA strain Beijing/A as the test article. 50 µl each of 1% mouse α-H3 latex particles, 1% goat α-rabbit latex particle control and assay diluent to serve as a no latex control were aliquotted into separate microfuge tubes. 100 µl of a 1:1000 dilution of H1N1 FluA was added to each (final dilution 1:1500.) All samples were incubated at 37° C. and shaken at 200 RPM for 30 min. Samples were subsequently 0.2 µm filtered and run on the FluA test. FIG. 2 clearly illustrates that H1N1 virus is neither removed by the anti H3N2 latex nor by the control latex confirming that the assay is indeed hemagglutinin serotype specific.

Example 3

Prophetic Outcome of Avian Influenza (H5N1) Testing with an Anti-H5 Neutralization and Removal Reagent The sample containing the suspected H5 avian influenza virus is run on the Binax NOW Influenza A/B test. Both the control line and the Influenza A lines show color, indicating 1) the biological reagents are functional and give an Immunological reaction and 2) Influenza A antigen is detected in the sample.

The next experiment is done to determine if Influenza A type H5 is in the sample. Two aliquots of the sample are mixed separately with a control latex reagent (a monoclonal antibody not directed to influenza virus coated onto 0.8 micron latex particles) and a test reagent (a monoclonal antibody anti-H5 coated onto 0.8 micron latex particles). The samples are incubated at 37 C for 30 minutes with mixing ($\leq 200$ rpm). The particles are separated from the liquid by either filtration or centrifugation. The supernatant liquid is then run on the Binax NOW Influenza A/B tests. If Influenza A (H5) is contained in the sample it is anticipated that the reactivity of the sample with the Influenza A test line will be less than the intensity of the aliquot, which was reacted with the control latex. Or the signal of the sample aliquot reacted with the anti-H5 latex may disappear altogether.

| Binax NOW Influenza A/B | Control Reagent | Anti H5 Reagent |
|---|---|---|
| Signal on the Control Line | + | + |
| Signal on the Influenza A Line | + | Negative, or less color than the control latex |

INCORPORATION BY REFERENCE

The contents of all cited references (including literature references, issued patents, published patent applications and GenBank Accession numbers as cited throughout this application) are hereby expressly incorporated by reference in their entireties.

EQUIVALENTS

Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations. Such equivalents are intended to be encompassed by the following claims.

What is claimed is:

1. A method, comprising a) contacting a sample comprising a pathogen with a first antibody specific for a variant-specific portion of the pathogen, wherein a pathogen-first antibody complex is formed if the variant-specific portion is present on the pathogen in the sample;

b) removing the pathogen-first antibody complexes from said sample, if present;

c) contacting the sample with a second antibody specific for a nonvariant-specific portion of the pathogen, wherein a pathogen-second antibody complex is formed if the pathogen is still present in the sample; and d) detecting the presence or absence of the second pathogen-antibody complexes; wherein the absence of said second pathogen-antibody complex indicates that the pathogen is of the variant for which the first antibody is specific.

2. The method of claim 1, wherein the pathogen is influenza type A.

3. The method of claim 2, wherein the first antibody is selected from the group consisting of: an anti-H3 antibody and an anti-H5 antibody.

* * * * *